(12) United States Patent
Toledano

(10) Patent No.: US 6,500,673 B1
(45) Date of Patent: Dec. 31, 2002

(54) ELECTROSTATIC DEVICE AND METHOD FOR IMMUNOLOGICAL DETECTION

(76) Inventor: Jacques Toledano, 55, rue des Orteaux, F-75020 Paris (FR)

( * ) Notice: Subject to any disclaimer, the term of this patent is extended or adjusted under 35 U.S.C. 154(b) by 0 days.

(21) Appl. No.: 09/744,578

(22) PCT Filed: Jul. 28, 1999

(86) PCT No.: PCT/FR99/01868

§ 371 (c)(1),
(2), (4) Date: Aug. 23, 2001

(87) PCT Pub. No.: WO00/07020

PCT Pub. Date: Feb. 10, 2000

(30) Foreign Application Priority Data

Jul. 28, 1998 (FR) .............................. 98 09599

(51) Int. Cl.[7] .............................. G01N 33/558
(52) U.S. Cl. .................. 436/514; 436/517; 436/518; 422/58; 422/68.1; 422/101; 435/285.2; 435/287.2; 435/204; 435/164; 435/672; 435/674
(58) Field of Search .................. 422/58, 59, 68.1, 422/186.26, 101, 102; 435/7.1, 283.2; 436/517, 514, 518; 204/164, 193, 415, 435, 660, 665, 670, 672, 674, 450, 456, 403, 252; 205/701

(56) References Cited

U.S. PATENT DOCUMENTS

| | | | | |
|---|---|---|---|---|
| 5,194,133 A | * | 3/1993 | Clark et al. .................. | 204/608 |
| 5,863,400 A | * | 1/1999 | Drummond et al. ........ | 204/415 |
| 5,916,156 A | * | 6/1999 | Hildenbrand et al. ....... | 600/347 |
| 6,051,380 A | * | 4/2000 | Sosnowski et al. ............ | 435/6 |
| 6,261,430 B1 | * | 7/2001 | Yager et al. ................. | 204/455 |

* cited by examiner

Primary Examiner—Long V. Le
Assistant Examiner—Gary W. Counts
(74) Attorney, Agent, or Firm—Young & Thompson

(57) ABSTRACT

The invention concerns a device and a method for ultrasensitive detection comprising an electrically inert porous sheet sandwiched between two positively charged fine electrodes. The invention uses the capacity of the electrodes, resulting from their powerful electrostatic properties, for sensing marked antibody complexes related to antigens detected in the sample, and to leave marked antibodies non-complexed with said antigens free. The method consists in depositing a sample droplet on the porous material sheet upstream of the electrodes and in detecting downstream of the electrodes, in a signal-zone, the possible presence of an antigen-antibody complex which has diffused in the porous material. The invention is useful for detecting some millipicogrammes of antigen per milliliter of sample.

28 Claims, 4 Drawing Sheets

ELECTROSTATIC DEVICE AND METHOD FOR IMMUNOLOGICAL DETECTION

The devices and methods of the prior art for performing precise immunological diagnoses generally use devices having most often already been the object of an immunological preparation (by immobilization of a first antibody). Thus the wells of the plates used in the ELISA type processes comprise in general a coating comprising first antibodies to capture an antigen, which will then be recognized by a second antibody, the whole being then revealed by a third anti-immunoglobulin antibody. The good practice of this process requires at least six washings and three hours of incubation.

Rapid tests have appeared during the 1980s, that use microballs previously clad with a first antibody and which migrate on a nylon surface to come to rest ultimately on a first line (presence of antigens) of second antibodies, for stopping in all cases on a second line of third antibodies. The whole takes place in several minutes, using a minimum of 7 nanograms of antigen per milliliter of specimen. This process does not permit detecting serum antibodies.

The object of the present invention is no longer an electrophoresis which is characterized by a more or less prolonged migration between two electrical poles (one at the beginning and the other at the end), as a function of molecular weight of different proteins. There exist more or less sophisticated gel techniques conducted between two electrodes and which permit separating a group of proteins in different bands according to their molecular weight.

The present invention has for its object to overcome the insufficiency of sensitivity of the known methods, in particular to provide a process permitting obtaining a qualitative or quantitative signal of the presence, at infinitesimal concentrations, of a substance in fluids of a specimen, even if it is not constituted by a nucleic acid. The so-called PCR (polymerase chain reaction) technique detects very small quantities of fragments of chromosomic material (RNA or DNA). It is not capable of measuring proteins such as new generations of tumoral markers or cytokenes circulating at quantities that can be less than a picogram per milliliter (a billionth of a gram). The immunological techniques, even the most sensitive such as radioimmunoanalysis, do not permit it.

The process according to the invention is applicable to the detection of any analyte that may be contained or adapted to be included in a fluid or a liquid which can react with a specific ligand to form a complex, the analyte or the ligand or both being carriers of electronic charges which are neutralized, or even reverse in the complex when the latter is formed. It is characterized in that:

the fluid or liquid is caused to migrate, after placing it in contact with the specific ligand, in an electrically inert porous material interposed between opposite surfaces of two electrically charged electrodes of the same polarity, and there are detected in the liquid that has migrated into the porous material between the two electrodes, those components, analyte, ligand or complex, which were not captured by the electrodes.

Needless to say, the total volume of fluid or liquid used, which is that contained in the dissolved condition of one of said components or both, particularly as a result of their possible mixing, must be sufficient to permit its diffusion in the porous material to the place where the detection is carried out.

According to the nature of the constituent detected, or not detected, therefore depends the conclusion that can be drawn as to concentration. In a preferred embodiment of the method according to the invention, one of the constituents, for example the ligand, is marked. It is for example an antibody which carries free $NH_2$ groups, therefore positive charges (the analyte being thus an antigen), and if the electrodes are negatively charged, the detection of the marker in the fluid or liquid having migrated into the porous material between the electrodes will show that the antibody is engaged in a complex, hence that the antigen was present in the original liquid or fluid. Thus following the antigen-antibody reaction, the $NH_2$ groups of the antibodies are masked in the formed complex, the positive charge of the antibody being thus neutralized, the antigen-antibody complex being again, as the case may be, able to have a negative polarity. On the contrary, the absence of detection will translate into the absence of the antigen in the fluid or liquid studied. Thus the marked antibodies which have not encountered "partners" are thus captured and blocked by the negatively charged electrodes.

Other examples show in what follows this description, important possibilities offered by the invention. But for good understanding of the invention, it may be useful to define the expressions "analyte" and "ligand", as used in the present description. Thus, the application of the invention is not limited to the detection of analytes constituted only by antigens or antibodies, even if it is in this connection that the invention will be most often used.

By analyte, should be understood any molecule or entity which it is desired to detect, no matter what its nature: haptene, protein, antigen, antibody, nucleic acid fragments, substance, even a group of molecules having common characteristics, this analyte being adapted to give rise to a specific reaction with a ligand to form a complex adapted to take part in a reaction seeking to detect in a selective manner the presence or absence of the analyte in a fluid or a liquid, for example a fluid of biological origin.

In the case of an analyte constituted by an antigen, it will be appreciated that the antibody, which thus plays the role of the ligand, is the carrier of $NH_2$ sites which give it a positive polarity, giving rise to the possibility for this antibody to be captured by an electrode having negative charges, whether the latter is of electrostatic nature or the result of placing the electrode under voltage in the suitable direction. Naturally, the converse can also take place. It can happen, for example, that in other types of analyte-ligand couples, the polar group will be formed from a negatively charged group, for example a COOH group, which will be neutralized in the analyte-ligand complex that is formed.

Accordingly, the ligand can as needed be itself modified by a group giving it its properties, for example the required electrical polarity for its use in the method of the invention. This could, by way of example, be the case when the analyte is constituted by a DNA fragment, whose presence can be searched for in a liquid after it has itself been used in a complementary RNA detection test. In such a case, the DNA fragment will be for example rendered the carrier of a biotin group, the ligand thus acceptable to be used-being adapted to be constituted by avidine, carrying itself, as the case may be, a marker, for example colorimetric, fluorescent, chemiluminescent, radioactive or the like and, if there was further need, a supplemental group giving it an electrostatic charge, which could thus be neutralized during the production of the analyte-ligand complex whilst susceptible to being formed, via the biotin-avidine reaction. Or else the analyte could be constituted by a DNA fraction and the ligand by a DNA probe itself marked by an enzyme, particularly peroxidase, by means of spacer arms produced by means of heterobifunctional systems, for example of the (DNA (FMCC)-peroxidase (SPDP) type.

Preferably, the analyte is in solution in a liquid or a fluid. But for example when the analyte consists of an antigen, it can also be contained for example in a biopsy or mucous fragment. But it then should be extracted by, or carried in, the liquid which will then migrate in the porous material between the electrodes.

As to the "porous" material, it must necessarily be meant by this expression any material permitting to propagation or diffusion of a liquid through its mass, when it has been moistened with this liquid. It could be constituted of any open pore material, fibrous material or which can behave as an absorbent, etc . . .

As to the electrodes, use can be made of any material adapted to be electrically polarized or electrostatically charged. Numerous materials in the form of thin sheets are available commercially: see for example the chapter beginning at page 53 of the catalog "DIMACEL Compounds and Related Electrostatic Packaging".

Those skilled in the art could obviously think of numerous different applications for the invention. This will be the case for any detection of a predetermined substance or "analyte" using a highly specific reaction with a corresponding "ligand". It will in all cases be possible, without the exercise of invention and if the need arises, to modify one of the constituents of the reaction to give it a polarity which will be neutralized, or even reversed in the final reaction product, wherein the method of the invention can also be applied to it. Similarly, those skilled in the art will in each case be able to adapt the method of the invention, for example to choose polarities to be given to the electrodes to render it operational for the detection of any analyte adapted to form a specific compound with a given ligand, when this formation is also accompanied by a neutralization, or even a reversal of the electric charge, either of the analyte, or of the ligand.

Thus more generally, when the polarities of the charges carried by the ligand and those of the electrodes are of opposite sign, the complex is detected in the liquid having migrated between the two electrodes when the initial having migrated between the two electrodes when the initial liquid contained the analyte.

Furthermore, when the polarities of the charges carried by the ligand and that of the electrodes are of the same sign and the polarities of the charges carried by the analyte and the complex itself are of opposite sign, there will be detected only the possible excess of ligand initially used when the analyte was initially present.

As has already been mentioned, it is advantageous that the ligand bear a marker, in particular a marker transformable into a colorometric, fluorescent or chemiluminescent signal and that the signal zone comprise a detector of the marker, in the signal zone that the liquid reaches that has migrated through the porous material, between the electrodes.

The signal zone is itself preferably formed in a porous material in contact with that which is interposed between the electrode, so as to permit access in the signal zone to the liquid having migrated first through the porous material interposed between the electrodes, and then through the porous material comprising the signal zone.

In one of its preferred embodiments, the method according to the invention thus uses the electrical attraction or repulsion exerted by two or more electrodes (preferably thin and flat), on one of the constituents of the analyte-ligand couple, for example on immunoglobulins (lg) accordingly as the immunoglobulins are bound or not to their specific antigen. A microdrop of specimen to be tested is disposed on the porous material, itself generally formed by a thin sheet, upstream of the latter or in the upstream region of the electrode pair, the drop of specimen being then absorbed immediately by the porous sheet, often an insulating paper. Then there is deposited a volume of marked antibody solution which will mix with the previously deposited drop of specimen. If the antigen that is sought is present in the drop of specimen, it will be rapidly captured by the marked antibodies. The electrodes will then differentiate between an antibody complexed with the antigen and an antibody which is not encountered antigen in the droplet, in particular when traversed by a negative electric current. In this case, the electrodes capture the $NH_2$ sites (positively charged) of the immunoglobulins which are not bonded to an antigen, and permit migration of the immunoglobulins (lg) whose $NH_2$ site is this time saturated and masked by an antigen in the porous sheet, between the two electrodes, up to the signal zone in which they can be detected and measured, when they have first been prepared before the determination (conjugated with an enzyme or a radioactive marker or any other means).

But these electrodes can also be positively charged or be traversed by a positive current, this time repelling the $NH_2$ sites of the immunoglobulins (lg) that have remained free from any bonding to an antigen. They will on the other hand capture the lg+antigens complexes which all have a sufficient number of negative charges, thus captured by this positive electrode. There thus occurs an inversion of the signal at the end of preparation: the signal is supplied only by the lg remaining free from any antigen.

Combinations of pairs of electrodes can also be used, associated with the porous material, in particular when it is sandwiched successively between a first pair and then, downstream of the latter, with a second pair of electrodes, the electrodes of this second pair being also charged and of identical polarities to each other, but of a sign opposite that of the polarities of the electrodes of the preceding pair, the detection being then carried out upstream of the second pair of electrodes, after the liquid has migrated through the porous material first through the first, then through the second pair of electrodes. This procedure thus permits also semiquantitative dosage, to the extent that the first pair of electrodes can retain only a predetermined quantity as the case may be, either the marked ligand, or of the complex formed, the final detection thus indicating only the excess as the case may be, either of the complex formed, or of the analyte initially present in the fluid or liquid that is studied.

Preferably the first pair of electrodes is of a sign such that, and is calibrated so as to trap a predetermined maximum quantity of the analyte in the form of an analyte-ligand complex, and there is detected downstream of the second pair of electrodes the excess of analyte which the fluid or a liquid initially contained.

This thus permits practicing semiquantitative determinations: the negative electrodes capture all the free immunoglobulins and the positive electrodes, which are smaller, capture only a portion of the lg+antigen complexes, this portion of the complexes corresponding to the physiological quantity of antigen that is not to be exceeded. If there is excess of this antigen, the positive electrodes could not capture all the complexes formed and a signal would thus be given, indicating the excess of this antigen beyond the physiological quantities.

An important advantage of the invention is the rapidity of determination. Between deposit of the specimen of the marked antibody solution, and the appearance of the result, takes hardly more than 5 to 10 seconds. The reason is that the attraction or repulsion of the antibodies is instantaneous, whilst if this reaction were entirely immunological (attraction of the complex antibody+antigen by a second antibody preliminarily fixed for example), an incubation would be necessary. Thus, the immunological reaction takes place in the insulating or electrically inert porous sheet immediately after the deposit. This immunological reaction can be accelerated by a factor of 10,000 times by the addition of suitable reagents (such as polyethylene glycol 8000 for example). The reaction which then takes place between the electrodes is thus not immunological but rather electrical, and hence instantaneous, which gives to this invention an essential quality for emergency determinations (for example, myocardial enzymes during infarction, forecast of an imminent embolism by determining D-Dimere or coagulation factors after bone surgery or in phlebitis, etc . . . ).

It is important that the antibodies comprise before the reaction free $NH_2$ groups. It is thus preferable that the antibodies remain monomers and that the marking takes place without the production of aggregates or polymers of the antibodies using the free $NH_2$ groups. In case of the formation of polymers or antibody aggregates, the $NH_2$ sites of the aggregated antibodies risk being masked, which will reduce correspondingly their capacity to be captured, particularly by the negative electrodes. The process could nevertheless be used, but with less sensitivity, to the extent the antibodies comprise a sufficient number of $NH_2$ groups adapted to intervene in the antigen-antibody reaction or, in the absence of antigen, to be captured in a sufficiently energetic way.

The preceding situation must in a very preferred way be avoided. Moreover, the marked antibodies (or other marked ligands) must be exempt from any free marker, even traces thereof, above all if there is involved an enzyme adapted to modify a substrate (or group of molecules forming a substrate). During production, for example, of conjugated antibodies marked with peroxidase by known techniques, it will be generally required to proceed with a purification of the marked antibodies by several molecules of peroxidase by techniques also known, particularly by chromatography of the reaction product so as to retain only the peaks of elusion containing the marked antibodies by several molecules of peroxidase and to eliminate all the others, plus those containing molecules of free peroxidase.

The marking of the monomeric antibodies can be carried out according to a very high ratio of molecules of marking per molecule of antibody, which can reach a value of 5. Recourse could also be had to mixtures of monoclonal antibodies, all marked, but recognizing epitopes respectively distinct from the antigen to be detected, which will increase all the more the sensitivity of detection.

The extreme sensitivity of the process in a number of its applications is due to several reasons:
  the materials used are all inert (porous material or electrodes) and do not fix any molecule of a protein as do the ELISA methods responsible for important background noise which prevents sensitive measurements. Foreign protein or foreign antibody can be fixed, which gives rise to the total absence of background noise.
  the signal zone contains the most sensitive reagents and the most rapid to react with the marking of the antibodies arrived there
  finally, the high sensitivity of the electrodes does not leave any of the "trappable" antibodies free, but above all does not trap any "non-trappable" antibody molecule adapted to give the signal. What can give the slightest signal can only correspond to a marked antibody and not to background noise.

In the present invention, it is not only a matter of separating or causing to migrate differentially the different molecular weights; it is moreover a matter of detecting or rejecting immunoglobulins according to whether they are bonded or not to their specific antigen. The molecular weight plays no role because the technique works perfectly as well with Fab fragments from IgG (the lightest) as with IgM supposed to be heavier.

In the present invention described here, the electrodes do not support any reaction. They play only, during the short instant in which a fluid migrates through the porous material, their electrical role of repulsion or attraction. This is the result of the migration of the fluids after passage between these electrodes, which supplies a signal, and not the electrodes.

As a modification, the ligand—or analyte—is deposited dry on a predetermined region of the porous material, in a region essentially upstream of the electrodes, the fluid or liquid presumed to contain the analyte—or the ligand—being introduced into this zone of the porous material.

For example, it is the analyte which is deposited in said predetermined region essentially in a region upstream of the electrodes. Preferably, it is also the analyte which is the carrier of the electrical charges, the fluid or liquid presumed to contain it being thus introduced into the region where the ligand is deposited; after possible in situ production of the complex, a separate dose of the analyte itself is reintroduced into the same region, the latter being this time marked, and the possible presence of the marked analyte is detected in the liquid having migrated between the electrodes.

The invention also relates to a device for the detection of an analyte adapted to be contained in a liquid, by reaction with a specific ligand of the analyte to form a complex, the analyte or the ligand or both being carriers of neutralized or even opposite electric charges in the complex when the latter is formed, this device comprising:
  at least one pair of two electrodes provided with surfaces which face each other and are electrically charged, with identical polarities, or adapted to be thus charged;
  a porous material, itself electrically inert, interposed between the surfaces and permitting the diffusion within it, between said electrodes, of the liquid adapted to be deposited in a free region of this porous material, essentially upstream of its path of migration through this porous material;
  means in combination with this porous material permitting the detection in the liquid having migrated through the latter, between said electrodes, of those of these components, analyte, ligand or complex, which have not been detected by the electrodes.

Preferably, the electrodes are formed of sheets that are statically charged or adapted to be thus charged and the porous material is itself formed of a sheet sandwiched between the two electrodes, this porous sheet extending downstream of said electrodes relative to the direction of migration and comprising in the external portion of the detection means, the constituents that have migrated.

This device is preferably provided with means for detecting a marker carried by one of the reagents, for example the ligand.

The means associated with said material or electrically inert porous sheet, are themselves preferably constituted by a porous sheet in contact with the first and through which can diffuse the liquid having migrated through the first to come into contact with the indicator contained in this second sheet.

In the description which follows, reference will be made more particularly to the situations arising the most frequently, for which the method and device of the invention are called upon to apply, those of the detection of particular antigens by predetermined specific antibodies (or vice versa).

Figure 3:
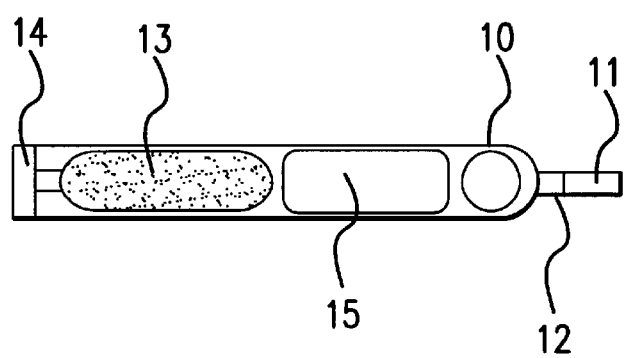
FIG. 3 shows the device accompanied with a pipette.
Figure 4:
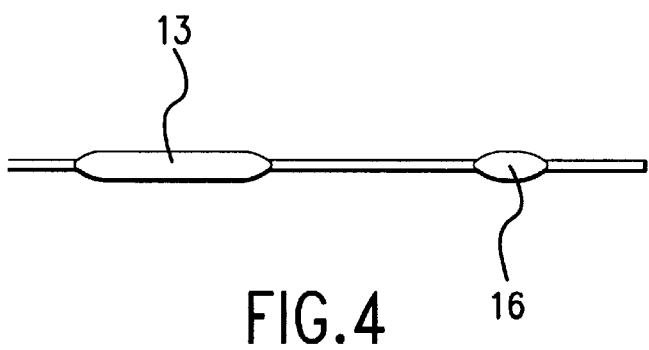
FIG. 4 is a side view of a pipette.

In one of its preferred embodiments, the device of the invention is comprised (FIGS. 1 and 2) of two electrodes 1 that are very thin (sheets), separated by a leaf of porous material 2 that is electrically inert, of any material (paper, nylon, nitrocellulose, etc . . . ). The upper electrode is perforated (opening 3) adjacent one of its ends to expose a region of the porous material which will receive in the first instance the drop of specimen to be tested and in a second instance the solution of marked antibodies or immunoglobulins specific to the sought antigen. This solution is contained in the pipette, which, preferably, accompanies the device (FIGS. 3 and 4). As soon as the drop is deposited, it behaves like a contactor between the electrodes which will then play their selective role to the extent the fluids migrate between them, through the porous sheet, and relative to the electrodes beyond their opposite end 5. The marked antibodies or immunoglobulins which have not been captured by the electrodes are thus detected in a region 7 in a material adjoining the preceding porous material or in communication with it, into which can also diffuse the liquids, even in an extension of the sheet of porous material, downstream of the electrodes. In its upstream region, adjacent the opening 3 where the specimen has been deposited, is located a small single zone 6 also receiving fluids in all cases (absence or presence of antigens). By becoming colored or by emitting any signal, it attests to the good conservation of the reagents and permits in the case of measurements carried out with a suitable apparatus, determining the difference between the quantity of marking before and after passage between the two electrodes. This small signal zone can also be on the other side of the device. It follows that the portion of electrode which extends between the opening 3 and its upstream end is very short, for example of the order of a millimeter, such that this portion can at most capture only a minimum proportion of the space in question. But it also follows that the location where the deposit of the reagents takes place could also of course be entirely upstream of the pair of electrodes, such that any false reaction will be avoided, even the least, concerning the "control quality for good conservation of reagents".

Figure 1:
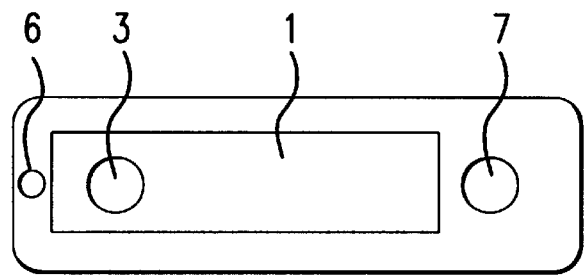
FIG. 1 is a top plan view of the device.
Figure 2:
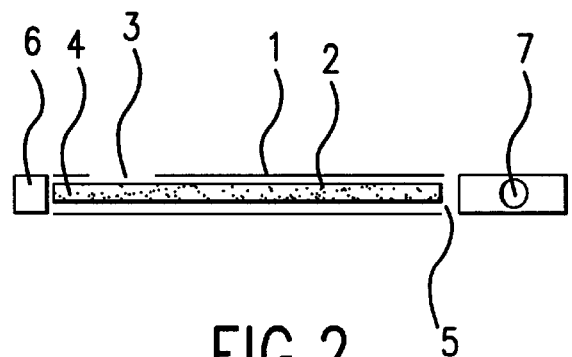
FIG. 2 is a cross sectional view of the device.

FIG. 1 is thus a top plan view and FIG. 2 a cross-sectional view of the device in which the reference numerals designate respectively:

1—Positively charged blades of electrodes.

2—Porous material in contact with the internal surfaces of the blades 1, which can absorb fluids from the specimen to diffuse them from the opening 3 towards regions 3 and 4.

3—Opening in the upper electrode for depositing a drop of specimen on the porous sheet.

4—Outlet to quality control for good conservation of reagents.

5—Outlet of the fluids after migration between the charged blades toward the results zone.

6—Signal zone for control/quality.

7—Signal zone for the result.

The size of the device can be of the same order of magnitude as the chip on a credit card. It can be inserted in a flat housing having approximately the thickness and the format of a credit card. The housing is thus provided with an opening in line with the opening 3 and with a reading window in line with the signal zone. In another embodiment of the invention described later, this opening and this window can even coincide. The device can also be inserted in a strip adapted to be inserted in a quantitative reader such as glycemia readers. In this case, the device does not require an integral electrical source, because by inserting it into the reader just before deposit of the specimen, the device benefits, by means of two contacts, from the electrical energy of the reader, precisely as for credit cards (which do not have their own source of electricity). Moreover, the electrical source, beyond a conventional microbattery, can be more simply a microdetector of the solar type which requires proceeding to detections or determinations under a light source or out in the light. Finally, certain electrodes based on hydroxyapatite are capable of offering a powerful electrostatic property, without having recourse to an electrical source.

The device can also be inserted at the end of a strip which will be simply immersed in the tube containing the marked antibody solution, after preliminary deposit of the droplet of specimen on the porous material through the opening 3. It naturally follows that in this type of device, all its parts, except the emplacement of the porous mass to which the opening 3 gives access, must be isolated in a sealed manner from the marked antibody solution (or from any other marked ligands).

There could also be formed a series of these devices, which will then be integrated into automata capable of thus treating tens of specimens at the same time.

The device of the invention is preferably associated with a pipette—or micropipette—capable of taking up a predetermined volume of the specimen containing the possible analyte and with a device adapted to deliver an also predetermined volume of the ligand. The micropipette must be precise, particularly graduated, capable of taking up a certain measured quantity of specimen (several microliters) and to deposit it on the porous material, through opening 3 of the device.

The micropipette and the device adapted to deliver the antibodies are preferably combined in a single device, the latter comprising at one of its ends a micropipette permitting taking up the measured volume of fluid or a liquid containing as the case may be the analyte and at its other end an ampule or the light containing the required volume for the reaction, of a solution of the ligand for example a marked antibody, this ampule being moreover provided with closure means that can be withdrawn or broken in a controlled manner to free the solution of the ligand, after introduction via the pipette of the volume of liquid to be studied in the porous material.

The marked antibody pipette is of transparent plastic whose plug is broken by simple rotation. It contains a sufficient volume of the antibody solution to moisten, progressively from the rear to the front, all of the porous material for separation and to bring the fluids to the signal zone. This pipette is often the single element of the device that is specific to the sought substance, because it contains the marked antibody specific to this substance. It is these antibodies which will be trapped or not by the electrodes. These latter are identical for all the devices and do not undergo any chemical or biological reaction much less an immunological one. They are thus universal and can be produced by mass production by robotized processes.

FIG. 3 is a view from above and FIG. 4 is a side view of such a pipette, particularly a micropipette (10) for taking up, in a flexible material that does not fix proteins (polypropylene or polycarbonate) comprising also the dose of the antibody as the case may be. It comprises, for example, at one of its ends, a ferrule 11 1 centimeter long and 1 mm in internal diameter, with a volume index (mark) 12 and, at its other end, a compartment 13 containing the antibody solution, for example 100 $\mu$l of an anti-HBs antibody for a determination of HBs antigen (for example in a volume of about 4–5 $\mu$l of sample to be tested). The compartment 13 is provided with a closure ferrule 14 which can be detached or broken. A label 15 carries the name of the antigen to be detected (for example "detection of HBs antigen"). A flexible bulb 16 (see FIG. 4) permits expelling the air and drawing up the desired volume of solution to be tested. By way of example, the pipette has a length of 5 cm and at its greatest transverse dimension, a width of 0.8 cm.

The first action will therefore be to take up several microliters of a specimen with the aid of the micropipette, to deposit this specimen in the opening 3, and then to break by rotation the closure ferrule or plug 14 located at its other end, on the side of the antibody solution, and finally to empty this latter into the opening 3.

In another modification, the antibody pipette (without the taking up micropipette) can be integrated as desired in a region of flexible material in the form of a reservoir which will empty (by pressure of the finger for example) into the opening 3 or in contact with the porous material approximately in this position as soon as the droplet of specimen will have been deposited with the help of a separately supplied micropipette.

Finally, the signal zone is arranged in a piece of porous material (white nylon for example) supporting reagents adapted to transfer the slightest molecule or marker for the antibodies which reach it, into a signal (colorometric or fluorescent or chemiluminescent or radioactive or the like). It is quite naturally at the end of the electrodes but it could be anywhere in the device, provided that the liquids reach it after their passage between the electrodes or over an extent sufficient to permit them to exercise the functions which have been described.

The invention therefore also relates to an assembly for immunological detection, characterized by three separate elements:

a transparent plastic element comprised:
  at one end, a micropipette for taking up several microliters of specimen (whole blood, serum, or any other biological fluid to be tested)
  at the other end, a pipette containing the marked antibody solution which is to be deposited following the specimen
a second element comprising the two electrodes separated by an insert porous or fibrous material interposed between these electrodes and an element of porous material impregnated with the reagents and adapted to absorb the fluids at the end of their migration between the electrodes.
finally, a third element serving as a support for the preceding. It could have the form of a perforated credit card to receive the specimen and the content of the pipette, as well as a window to expose the signal zone. The second element would thus be placed below the card. But this support could also have the form of a strip at the end of which is located the second element, so as to insert it easily into a reading device.

Figure 5:
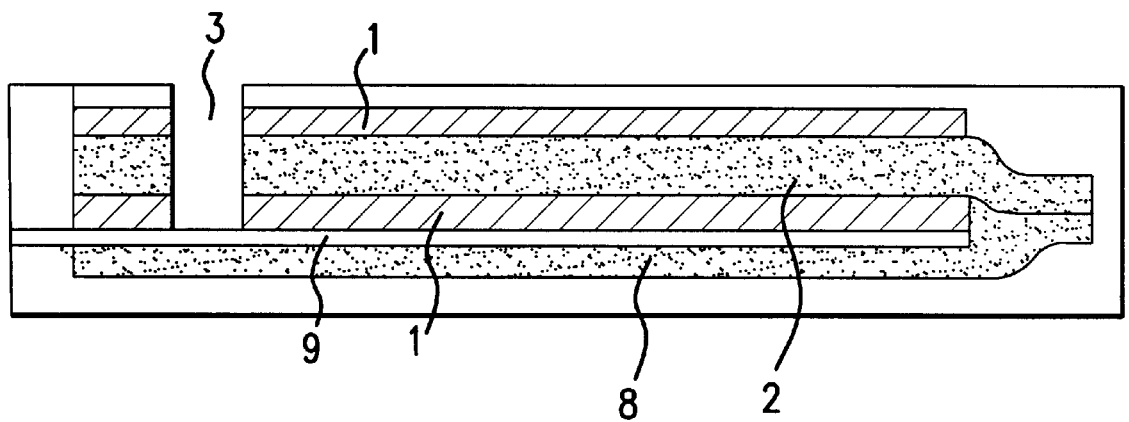
FIG. 5 shows a cross sectional view of the device with several modifications.

An interesting modification is shown in FIG. 5. According to this modification, the opening 3 which passes through the first electrode, also passes through the porous material and the second electrode of the same pair, the porous sheet being connected upstream of the electrodes to a second porous sheet 8 in which the liquid can diffuse that has migrated through the electrodes, this second sheet being flattened against the lower surface with the second electrode, opposite the inlet to the opening, and this by means of a transparent sheet 9, which is sealed, as the case may be adhesive, and defining the bottom of the opening. A second porous sheet could thus be provided with the indicator in the region located in line with the opening 3, and this so as to permit the "reading" of the reaction directed through the opening in which has been introduced the reagents.

The transparent sheet 9 serves both for sealing the opening 3 and for the supply of the signal zone below this transparent sheet. The fluids leaving upstream of the electrodes, are sucked up by the second porous sheet, toward this new signal zone. The coloration, for example, will be seen from above, through the transparent adhesive, in the vicinity of the same opening 3. This simplifies the device which no longer will have only a single opening to deposit the specimen and to permit the user to see the result in several seconds following, adjacent the same deposit. The only limit to this interesting variation concerns specimens that are particularly thick, colored, viscous which can trouble the reading of the result by transparency. But in this case the device can be arranged so as to permit the user to observe the signal on its opposite side (as small strips for the determination of glycemia). Recourse could also be had for example to a microray laser, this modification would thus be very attractive.

Figure 6:
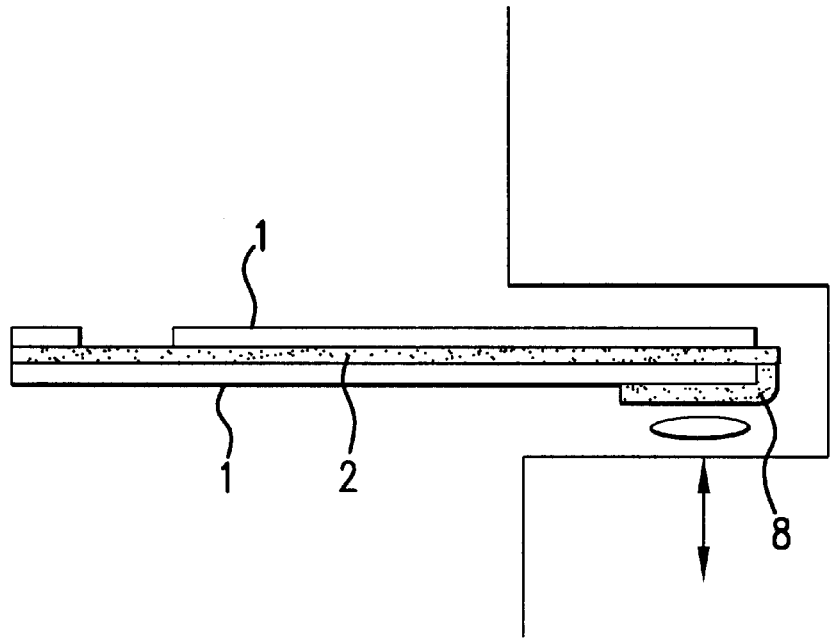
FIG. 6 shows a side view of the device with several modifications.

Still another modification of the device according to the invention is shown schematically in FIG. 6, the same elements being represented by the same reference numerals. Here again, the signal zone 7 is present on a second porous element in contact with the porous sheet 2, the signal zone being incorporated in an apparatus for quantification permitting measurement of the signal, particularly by means of the degree of adsorption of a laser ray.

The examples which follow plainly have no limiting character. Their only object is to give an appreciation of the variety of the possibilities offered by the process according to the invention. It will be evident that those skilled in the art can likewise devise numerous others.

1—Detection of the HBs Antigen of Hepatitis B in Serum

Material: A pipette of 100 $\mu$l of marked monoclonal antibodies Peroxidase concentrated to 2 micrograms/ml—a device (sheet of porous paper sandwiched between two negatively charged electrodes) whose signal zone contains tetra-methyl benzidine, with a Peroxidase substrate.

Protocol: there is deposited in the opening 3 of a volume of 4 $\mu$l of serum positive as to the HBs antigen (10 ng/ml), then 100 $\mu$l of a solution of antibodies.

Results: 10 seconds after deposition, the fluid has diffused toward the signal zone and the result can be read in the reading window, 5 seconds later, in the form of a pale blue coloration which darkens to intense blue in 5 seconds. Toward time: 20 seconds.

Tests of sensitivity: the same serum is diluted 1000 times: new content of HBs: 10 micrograms/ml. The same procedure is followed: the coloration appears with the same delay, but slightly less intense.

Further dilution 10 times: 1 picogram/ml. Blue coloration clearly visible but has required 10 seconds more to appear.

New dilution 10 times: 0.1 picograms/ml: blue coloration but has required an additional 30 seconds to become clearly visible.

New dilution 10 times: 10 millipicograms/ml: the coloration is pale blue but it has taken 1 minute longer to appear relative to the last test: total duration to have a signal with 10 millipicograms: 2 minutes. (blue coloration is clearly visible at the end of 5 minutes)

New dilution 10 times: 1 millipicogram/ml. Very slight coloration after 5 minutes. Invisible to the naked eye. Possibility of evaluation by well calibrated apparatus. The sensitivity is extreme: the system can detect for example several millipicograms of HBs antigen, namely several viral particles per specimen.

2—Semi-Quantitative Determination of D-Dimer in the Serum

The physiological quantity of D-Dimer is 0.4 micrograms maximum. It increases immediately before the fibrous lysis of a blood clot, announcing the risk of an embolism (bone surgery, pelvic surgery, cardiology, etc . . . ). This determination is of the predictive negative type, which is to say that 100% of the patients in which the tests are negative have no embolism, whilst 60% of the patients in which the tests are positive risk having an embolism. It is thus an excellent test to exclude the risk of embolism.

The problem which arises is to know how to neutralize 0.4 $\mu$g/ml of D-Dimer. To do this, recourse can be had to two pairs of electrodes respectively applied along the sheet of porous material, which is to say a first pair of negative electrodes (which will capture all the antibodies not bounded to D-Dimer) then a second pair of small positive electrodes (5 mm long) programmed or calibrated to capture the equivalent of 0.4 $\mu$g/ml of D-Dimer connected to their monoclonal antibodies.

Several serums will be tested
- a—Serum A: calibrated to 0.4 $\mu$g/ml of D-Dimer. The signal zone will be moistened in several seconds and no coloration will be produced even at the end of 5 minutes.
- b—Serum B: measured in the laboratory by ELISA: quantity of D-Dimer: 0.76 $\mu$g/ml: blue coloration which is first pale in 5 seconds and then clearly visible blue at the end of 20 seconds.
- c—Serum C from a patient which just had a pulmonary embolism: quantity of D-Dimer: 5.67 $\mu$g/ml: coloration intense blue, immediate, 1 second after the signal zone is moistened.

3—Detection of Serum Antibodies Against HIV1+2 Virus

Principle:

This time, the device is preliminarily prepared for this diagnosis, by depositing on the porous sheet, at the height of opening 3, peptides of HIV virus, the deposit having been dried before packaging the device. Conversely to the antigen determination, which uses the same support no matter what antigen is sought (the only variation is the antibody pipette marked specifically for the antigen sought), the detection of serum antibodies can, for a precise diagnosis, involve the preliminary preparation of specific supports carrying a dose of the antigen in question.

The antibody pipette contains 100 $\mu$l of monoclonal immunoglobulins marked by alkaline phosphatase, of very great affinity and highly specific to the viral peptides deposited in 3.

The signal zone contains substrates of alkaline phosphatase.

Operative mode:

Several microliters of seropositive serum are deposited on the region of the porous sheet comprising the antigen. If the specimen of serum is seropositive, the anti-HIV serum antibodies complex rapidly to viral peptides. The marked antibody deposited in the second instance do not find free viral peptides and will not be trapped by the electrodes (in this case: positive electrodes). They will therefore migrate toward the signal zone and will reproduce a coloration attesting to the zero positivity of the specimen.

The seropositive serum is diluted 1000 times and the above is repeated: blue coloration less intense than before.

This last solution of serum is diluted 100 times, namely to the total dilution of 100,000 times: blue coloration clearly visible, but after 2 minutes.

If the specimen is seronegative, the quantities of microliters deposited at 3 do not contain any serum antibody. The viral peptides first deposited on 3 will remain free. The marked antibodies deposit, in the second instance, gives rise to the immediate formation of marked antibody complexes+ viral peptides, complexes which will be trapped by the positive electrodes. There will be no coloration of the signal zone.

Test: total of the duration to have a signal with 10 millipicograms: 2 minutes (clearly visible blue coloration).

The above examples thus show the extreme sensitivity of the detection: 10 millipicograms of antigen or antibodies per millimeter of specimen if a calorimetric reading is used, one millipicogram if a more sensitive apparatus than the human eye is used.

In still another modification of the invention, the porous material comprises antibodies fixed in the introduction region for the reagents, upstream of the electrode pair, or at the level of the opening 3, and this to permit the detection this time of the corresponding antigens in a liquid or fluid to be studied. In this instance, the antibodies can be fixed to the porous material, for example by means of protein A, under conditions that do not disturb the fixation of the antigens to be detected.

The schematic drawings of FIG. 7 show the successive steps of a semiquantitative determination of antigens, which takes place upon their fixation to antibodies retained on the porous material (FIG. 7a), then their reaction with other antibodies, this time marked, also specific to the antigen.

In the example that follows, there is added to a given fluid or a liquid a possible excess of antigens relative to the normal. In this hypothesis, the quantity of antibodies retained in the region 3 of the porous sheet corresponds to that which permits the fixation of all the antigens contained in a predetermined volume of the fluid or liquid, for example a serum, when the antigen content of this fluid does not exceed a threshold value, corresponding for example to normality.

Figure 7A:
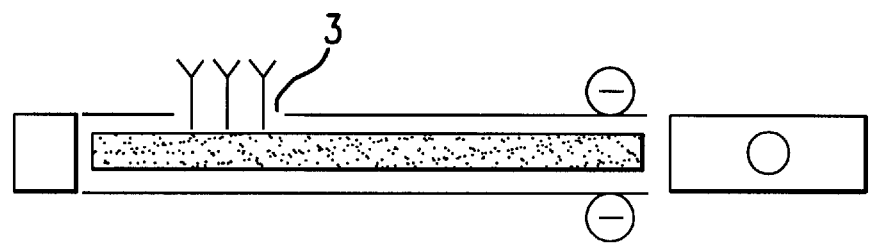
FIGS. 7a–7d show the successive steps of a semiquantitative determination of antigens.
Figure 7B:
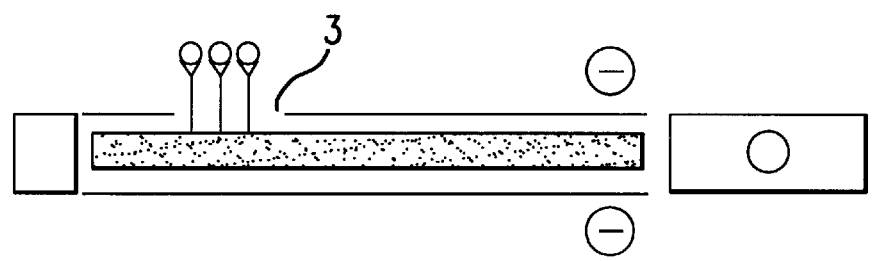

In this last case, all the antigens carried by the predetermined volume of serum will be fixed on the porous sheet (FIG. 7b).

Figure 7C:
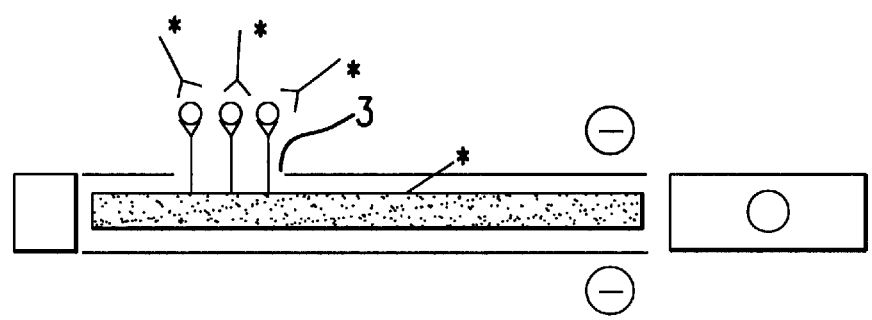

The marked antibodies then added, will in turn fix to the antigen molecules retained on the porous material, the possible excess of marked antibodies being then captured by the negative electrodes, such that no detection of marked antibodies can take place in the signal zone 7 (FIG. 7c). In other words, the absence of a detected signal means that the antigen content of the fluid or liquid tested included no excess antigens, beyond the predetermined threshold mentioned above.

Figure 7D:
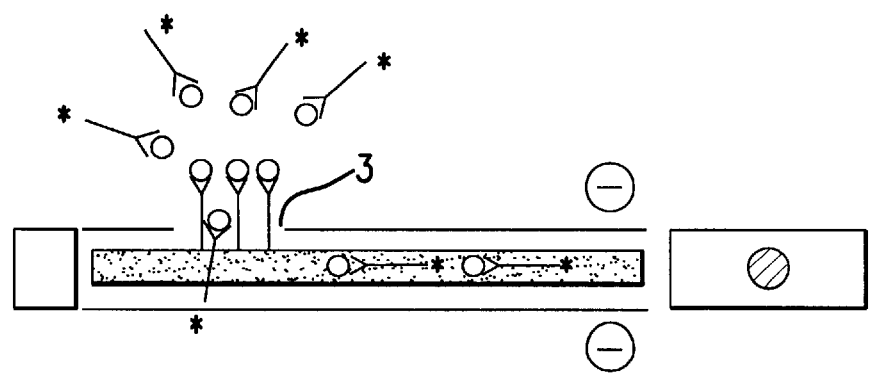

Moreover, if the serum contains an excess of antigens relative to the normal, the totality of the antigens of the predetermined volume of liquid deposited in the region 7 will no longer be retained by the support antibodies of the porous sheet. The addition of marked antibodies will thus give rise also to the production of antigen-antibody complexes that are not retained in the region of the opening 3. But these complexes cannot be captured by the negative electrodes. These marked antigen-antibody complexes, in excess, will thus defuse through the porous material and be detected in the signal zone 7, for example thanks to the coloration of a substrate if the marker was of an enzymatic nature (FIG. 7d). In other words, the detection of a coloration shows the existence of an excess of antigen in the initial liquid or fluid, exceeding the threshold value indicated above.

Figure 8:
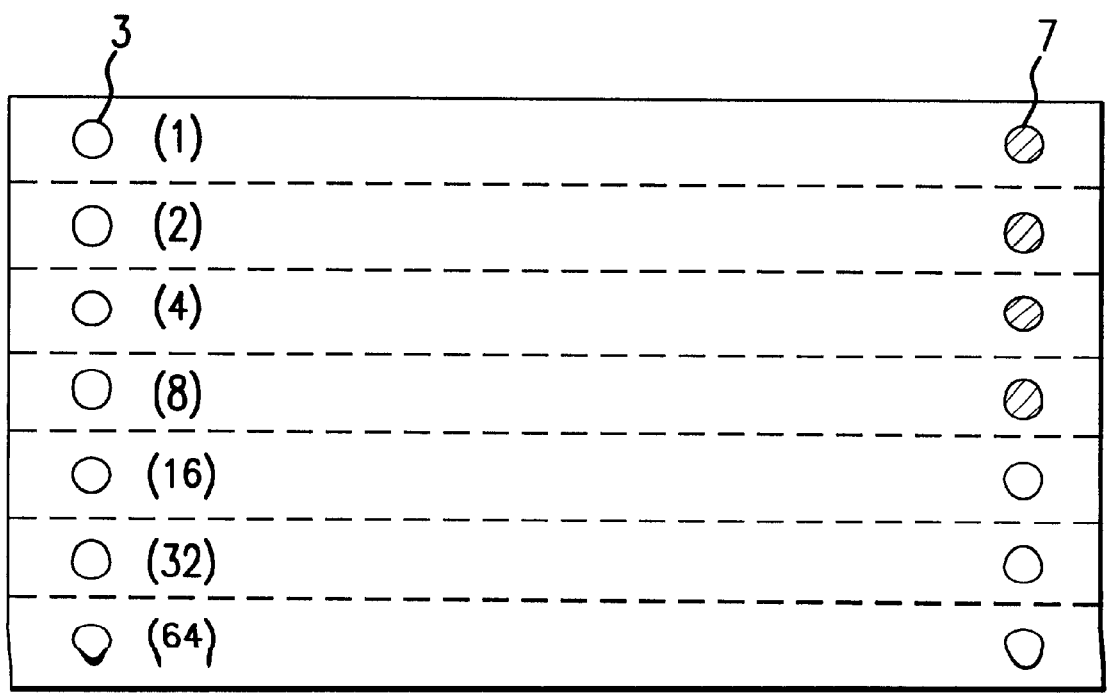
FIG. 8 shows a plurality of porous sheets or strips disposed side by side until acting with corresponding pairs of negative electrodes.

In another modification, the process according to the invention permits a semiquantitative determination of the content of antigens in a liquid or fluid relative to predetermined doses of antibodies. The schematic diagram of FIG. 8 shows one of the ways to proceed, for example by the use of a deposit of a device of the type in question comprising a plurality of porous sheets or strips disposed side by side and coacting with corresponding pairs of negative electrodes. Each strip of course corresponds also to a zone of deposit of a predetermined volume of the antigen solution and a signal zone for the detection of the marked antibody in an antigen-antibody complex which could not have been captured by the corresponding pair of electrodes. It naturally follows that the porous strips of the parallel devices are isolated laterally from each other such that the liquid diffusing longitudinally in one of them toward the corresponding signal zone, cannot at the same time diffuse laterally and invade the adjacent porous strips.

The semiquantitative determination, or even the quantitative determination, of the antigen content of a liquid or fluid relative to a given dose of antibodies, can thus be carried out with a device of this type, as the respectively increasing doses of antibodies will have been fixed at the outset to regions of the porous strips upstream of the corresponding pairs of electrodes (for example successively 1 dose, 2 doses, 4 doses, 8 doses, 16 doses, 32 doses, 64 doses (according to the numbers between parentheses in the schematic drawing of FIG. 8).

Predetermined volumes of liquid containing the antigen to be detected (the same for all the strips) are thus deposited in the regions 3 of the different strips. If the antigen is in excess relative to the quantity of antibodies (1 dose) retained on the first strip (upper portion of the schematic drawing of FIG. 8), only a portion of the supplied antigens is fixed. After addition of an excess of marked antibodies, the excess of antigens non-retained, and thus complexed by the marked antibodies in excess, will migrate toward the signal zone. A coloration is thus given to them. The same observation will again be made if the quantity of antigens contained in the predetermined volume of specimen will be further in excess relative to the two doses of antibodies retained on the second strip. There will similarly be observed a coloration of the corresponding signal zone. There will occur, nevertheless, a moment at which all the antigen contained in the volume of original specimen has effectively been fixed to the antibodies retained in the regions 3 by corresponding strips, which thus shows up even after the addition of great excess of marked antibodies, by the cessation of observation of a coloration in the corresponding signal zone. The same is true for the following strips whose regions 3 retain from the outset increasingly greater quantities of antibodies. In the diagram of FIG. 7, it will be seen that the threshold of equilibrium between the antigen content of the volume relative to the increasing quantities of antibodies retained on the strips, is between "eight doses of antibodies" and "sixteen doses of antibodies".

It follows that the last modifications of the process according to the invention are equally applicable to the semiquantitative measurement of an analyte relative to a given ligand, particularly as has been defined in claims 16–17. Similarly, the invention relates to modifications of the devices permitting the practice of these modifications of procedure. Particular reference is had to the modifications of the device defined in claims 27 and 28.

What is claimed is:

1. A process for the detection of an analyte contained in a fluid or a liquid, by reaction with a specific ligand to form a complex, the analyte or the ligand or both being carriers of neutralized electric charges, or opposite charges when the complex is formed, said process comprising:

causing said fluid or liquid to migrate, after contact with the specific ligand, into a first porous electrically inert material interposed between opposite surfaces of a first pair of electrically charged electrodes of the same polarities, and detecting in the liquid having migrated into the porous material between the two electrodes, said analyte, ligand or complex, which have not been captured by the electrodes.

2. The process according to claim 1, wherein the polarities of the charge carried by the ligand and those of the electrodes are of opposite sign, and the complexes detected in the liquid having migrated between the two electrodes when the initial liquid contained the analyte.

3. The process according to claim 1, wherein the polarities of the charges carried by the ligand and that of the electrodes are of the same sign and the polarities of the charges carried by the analyte and the complex are of opposite sign, wherein the process further includes the step of detecting an excess of the ligand which do not bind to the analyte and wherein the excess of the ligand is detected when the analyte was initially present.

4. The process according to claim 1, wherein the ligand carries a marker which is detected in a signal zone wherein the liquid migrates through the porous material between the electrodes.

5. The process according to claim 4, wherein the marker is transformable into a colorimetric, fluorescent or chemiluminescent signal, and the signal zone comprises an indicator of the marker.

6. The process according to claim 4, wherein the signal zone is formed from a second porous material, said second porous material in contact with said first porous material which is interposed between the electrodes, so as to permit access in the signal zone to the liquid having first migrated in the first porous material interposed between the electrodes, then into the second porous material comprising the signal zone.

7. The process according to claim 1, wherein the ligand is deposited dry on a predetermined region of the first porous material, in a region upstream of the electrodes, and wherein the fluid or liquid containing the analyte is introduced into said region of said first porous material.

8. The process according to claim 1, wherein:

the first porous material interposed between a preceding pair of electrodes, further comprises an extension beyond said first electrodes, said liquid or fluid is caused to pass between a second pair of electrodes supplied on opposite zones of said extension of the first porous material, the electrodes or this second pair being charged and of identical polarities to each other, but of a sign opposite to that of the polarities of the electrodes of the first pair, and the detection is carried out upstream of the second pair of electrodes, after which the ligand has migrated into said first porous material first through the first pair and then through the second pair of electrodes for semiquantitative determinations.

9. The process according to claim 8, wherein the first pair of electrodes is calibrated so as to trap a maximum predetermined quantity of analyte in the form of analyte-ligand complex, and their is detected downstream of the second pair of electrodes an excess of analyte.

10. The process according to claim 7, wherein the analyte carries electrical charges, wherein the fluid or liquid containing the analyte is introduced into the region of the deposited ligand, to form of the complex, thereafter a separate dose of the analyte is introduced into the region, wherein the second dose of the analyte is marked, and the presence of marked analyte is detected in the liquid having migrated between the electrodes.

11. The process according to claim 9, wherein the analyte is constituted by a predetermined antigen, the ligand by a specific antibody of the antigen, and the electrodes of the first pair of electrodes have a negative polarity.

12. The process according to claim 11, wherein the first pair of electrodes is calibrated to trap a quantity of an analyte ligand complex, the quantity of trapped antigen cannot exceed that corresponding to its normal content in the original liquid, or fluid, wherein the fluid is a biological fluid from a healthy subject, and the detection is only of the excess antigen relative to the normal content of antigen present in the original fluid or liquid.

13. The process according to claim 12, further comprising a step of detecting an excess in blood plasma of D-Dimer.

14. The process according to claim 1, wherein the analyte is an antibody, the ligand an antigen.

15. The process according to claim 14, wherein the polarities of the first pair of electrodes are of opposite sign to those of the antibodies.

16. The process according to claim 1, wherein the analyte is deposited in a region determined by the first porous material upstream of the electrodes, said region not permitting the retention of a dose of analyte exceeding a predetermined threshold value, a volume of solution containing an electrically charged ligand is deposited in said region whose polarity is opposite that of the electrodes, and the analyte ligand complex in the liquid having migrated between the two electrodes is detected such that the quantity of analyte initially deposited on said region will exceed the dose defined by the predetermined threshold value.

17. The process according to claim 16, wherein the analyte is an antigen and the region or predetermined regions of the porous material are coated with quantities of antibodies responsible for said threshold values.

18. A device for the detection of an analyte contained in a fluid or liquid by reaction with a specific ligand of the analyte to form a complex, the analyte or the ligand or the two being carriers of neutralized electric charges or opposite charges when the complex is formed, said device comprising:

at least one pair of electrodes provided with surfaces which face each other and are electrically charged, with identical polarities;

an electrically inert porous material, interposed between the surfaces and permitting diffusion, between said electrodes, of the liquid to be deposited in a free zone of said porous material, upstream of a liquid path of migration in said porous material; and means associated with said porous material for the detection in the liquid migrated into the porous material, between said electrodes, said analyte, ligand or complexes, which have not been captured by the electrodes.

19. The device according to claim 18, wherein the electrodes are in the form of sheets that are electrostatically charged, and that the porous material is in the form of a first porous sheet sandwiched between the two electrodes, the first porous sheet extending upstream of said electrodes relative to the direction of migration and comprising, in an external portion, said means for the detection.

20. The device according to claim 18, further comprising display means of a marker carried by the ligand.

21. The device according to claim 19, further comprised of a second porous sheet in contact with a first sheet and wherein the liquid migrates through the first and second sheets to come into contact with an indicator contained in the second sheet.

22. The device according to claim 18, further comprising an opening pierced in one of the electrodes and giving access to the porous material in the region upstream of said electrode, this opening being for the introduction of the fluid or liquid containing the analyte or ligand.

23. The device according to claim 22, wherein the ligand is incorporated in a dry state in the porous material in the same region as the opening.

24. Device according to claim 22, wherein the opening which passes through the first sheet also passes through the porous material and the second electrode of the same pair, the porous sheet being connected upstream of the electrodes to a second porous sheet wherein the liquid migrates through the electrodes, the second sheet being flattened on the under surface of the second electrode, opposite the inlet of the opening, by a transparent sheet, which defines a bottom of the opening, the second porous sheet being provided with an indicator in the region located in alignment with the opening, for reading of the reaction and introduction of agents directly through the opening.

25. The device according to claim 18, wherein said device is in combination with a pipette for removal of a measured volume of the fluid or liquid that contains the analyte, said pipettte including an ampule at one end for containing the volume required for the reaction, of a solution of the ligand, said pipette further includes a detachable closure means for dispensing the solution of the ligand, after introduction by the pipette of the volume of liquid to be detected in the porous material.

26. The device according to claim 18, further comprising a housing for enclosing said electrodes, said porous material and detecting means and a reservoir for containing a solution of the ligand, said housing comprised of elastic material or flexible material, to permit freeing and an introduction of the solution from the reservoir into the porous material by a pressure exerted on walls of the housing.

27. The device according to claim 23, wherein the zone in which the analyte is deposited permits the retention of only a quantity of analyte not exceeding a predetermined threshold value.

28. The device according to claim 27, wherein the analyte is an antigen and the zone or predetermined zones of the porous material are coated with quantities of antibodies responding to said threshold values for retention of corresponding antigens.

* * * * *